United States Patent
Segi et al.

(10) Patent No.: US 11,065,423 B2
(45) Date of Patent: *Jul. 20, 2021

(54) BALLOON CATHETER

(71) Applicant: ASAHI INTECC CO., LTD., Nagoya (JP)

(72) Inventors: Kazuteru Segi, Nagoya (JP); Takeharu Katsurada, Nagoya (JP); Yuta Kubo, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 224 days.

This patent is subject to a terminal disclaimer.

(21) Appl. No.: 16/005,757

(22) Filed: Jun. 12, 2018

(65) Prior Publication Data
US 2018/0289933 A1      Oct. 11, 2018

Related U.S. Application Data

(63) Continuation of application No. 14/978,345, filed on Dec. 22, 2015, now Pat. No. 10,022,522.

(30) Foreign Application Priority Data

May 1, 2015   (JP) .................................. 2015-094088

(51) Int. Cl.
*A61M 25/10* (2013.01)
*A61M 25/00* (2006.01)
*A61M 25/01* (2006.01)

(52) U.S. Cl.
CPC ........ *A61M 25/10* (2013.01); *A61M 25/0054* (2013.01); *A61M 25/0102* (2013.01);
(Continued)

(58) Field of Classification Search
CPC .......... A61M 25/10; A61M 2025/1061; A61M 2025/1084; A61M 2025/0063;
(Continued)

(56) References Cited

U.S. PATENT DOCUMENTS

| 4,362,163 A | 12/1982 | Krick |
| 4,586,923 A | 5/1986 | Gould et al. |

(Continued)

FOREIGN PATENT DOCUMENTS

| CA | 2 468 108 A1 | 6/2003 |
| EP | 0 578 777 B1 | 1/1998 |

(Continued)

OTHER PUBLICATIONS

Feb. 19, 2019 Office Action issued in Japanese Patent Application No. 2018-095087.

(Continued)

*Primary Examiner* — Brandy S Lee
*Assistant Examiner* — Hong-Van N Trinh
(74) *Attorney, Agent, or Firm* — Oliff PLC (57) ABSTRACT

A balloon catheter includes an inner shaft with a distal variant portion and a proximal variant portion. A bulged portion is provided at the distal end of a reinforcement member, and the bulged portion is configured to move in an axial direction between the distal variant portion and the proximal variant portion. Thus, the balloon catheter may smoothly pass through a curved blood vessel with improved kink resistance of the reinforcement member.

6 Claims, 8 Drawing Sheets

(52) U.S. Cl.
CPC ............... *A61M 2025/0063* (2013.01); *A61M 2025/0183* (2013.01); *A61M 2025/1061* (2013.01); *A61M 2025/1084* (2013.01)

(58) Field of Classification Search
CPC .......... A61M 25/0102; A61M 25/0054; A61M 2025/0183; A61M 25/0133; A61M 25/0147; A61M 25/1006
See application file for complete search history.

(56) References Cited

U.S. PATENT DOCUMENTS

| | | | |
|---|---|---|---|
| 5,147,315 A | 9/1992 | Weber | |
| 5,176,637 A | 1/1993 | Sagae | |
| 5,217,482 A * | 6/1993 | Keith | A61M 25/0662 604/102.02 |
| 5,242,396 A | 9/1993 | Evard | |
| 5,312,340 A | 5/1994 | Keith | |
| 5,336,178 A | 8/1994 | Kaplan et al. | |
| 5,417,658 A | 5/1995 | Loney et al. | |
| 5,487,757 A | 1/1996 | Truckai et al. | |
| 5,514,093 A | 5/1996 | Ellis et al. | |
| 5,545,133 A * | 8/1996 | Burns | A61M 25/10187 604/99.04 |
| 5,649,908 A | 7/1997 | Itoh | |
| 5,690,613 A | 11/1997 | Verbeek | |
| 5,823,995 A * | 10/1998 | Fitzmaurice | A61M 25/104 604/103.09 |
| 6,436,090 B1 | 8/2002 | Sanchez et al. | |
| 6,482,221 B1 | 11/2002 | Hebert et al. | |
| 6,702,781 B1 | 3/2004 | Reifart et al. | |
| 6,733,473 B1 | 5/2004 | Reifart et al. | |
| 7,815,627 B2 | 10/2010 | Von Oepen et al. | |
| 8,088,121 B2 | 1/2012 | Nishide et al. | |
| 8,403,885 B2 | 3/2013 | Arana et al. | |
| 9,913,966 B2 | 3/2018 | Katsurada et al. | |
| 10,022,522 B2 | 7/2018 | Segi et al. | |
| 2002/0142119 A1 | 10/2002 | Seward et al. | |
| 2004/0006305 A1 | 1/2004 | Hebert et al. | |
| 2004/0019324 A1 | 1/2004 | Duchamp | |
| 2012/0226231 A1 * | 9/2012 | Nishigishi | A61M 25/0102 604/103.09 |
| 2012/0253447 A1 | 10/2012 | Hayasaka et al. | |
| 2012/0296367 A1 | 11/2012 | Grovender et al. | |
| 2014/0142506 A1 | 5/2014 | Prindle et al. | |
| 2016/0317789 A1 | 11/2016 | Segi et al. | |

FOREIGN PATENT DOCUMENTS

| | | |
|---|---|---|
| EP | 1 787 673 A1 | 5/2007 |
| EP | 2 389 973 A1 | 11/2011 |
| EP | 2 495 006 A1 | 9/2012 |
| EP | 2 859 908 A1 | 4/2015 |
| JP | 2012-020077 A | 2/2012 |
| JP | 2012-183127 A | 9/2012 |
| JP | 2013-090820 A | 5/2013 |
| JP | 2013090820 A * | 5/2013 |
| JP | 2013-106798 A | 6/2013 |
| JP | 2015-083028 A | 4/2015 |
| WO | 92/17236 A1 | 10/1992 |
| WO | 2014/141440 A1 | 9/2014 |

OTHER PUBLICATIONS

Nov. 7, 2019 Office Action issued U.S. Appl. No. 15/876,432.
Sep. 30, 2016 Search Report issued in European Patent Application No. 16155233.6.
Jan. 11, 2018 Office Action issued in Japanese Patent Application No. 2015-047146.
Aug. 2, 2016 Extended European Search Report issued in European Application No. 16153560.4.
May 11, 2017 Search Report issued in European Patent Application No. 17151391.4.

* cited by examiner

BALLOON CATHETER

CROSS REFERENCE TO RELATED APPLICATION

This application is a continuation of U.S. application Ser. No. 14/978,345 filed on Dec. 22, 2015 and claims priority to Japanese Patent Application No. 2015-094088 filed in the Japan Patent Office on May 1, 2015, the entire contents of which are incorporated by reference.

BACKGROUND

The disclosed embodiments relate to a balloon catheter to be inserted into a stenosis site inside a blood vessel for expanding the stenosis site.

Balloon catheters to be inserted into a stenosis site inside a blood vessel for expanding the stenosis site are known in the art. A typical balloon catheter includes a balloon as an expanding body, an outer shaft joined to the proximal end of the balloon, and an inner shaft inserted within the balloon and the outer shaft.

Further, it is known to provide a wire reinforcement member inside the outer shaft. This reinforcement member is intended to prevent the balloon catheter from kinking when inserted into the blood vessel and to provide improved maneuverability when an operator, such as a physician, inserts the balloon catheter into the blood vessel.

For example, Japanese Patent Application Laid-Open No. 2013-106798 (JP '798) discloses a balloon catheter with a wire member (a reinforcement member) inserted through an interior space of a middle shaft. A distal end side of the wire member is inserted through a fixing tube and a proximal end side of the wire member is fixed to a proximal end shaft.

However, there is a disadvantage in the balloon catheter of JP '798. The distal and proximal ends of the wire member (reinforcement member) are fixed with the fixing tube and the proximal end shaft, respectively. Therefore, when the balloon catheter is inserted into a curved blood vessel, the wire member (reinforcement member) cannot follow the curvature of the blood vessel smoothly and appropriately, resulting in the wire member being bent. Thus, the balloon catheter cannot be further pushed distally.

Accordingly, the disclosed embodiments provide a balloon catheter that includes a reinforcement member capable of following the curvature of a blood vessel, thus allowing for smooth passage of the balloon catheter through the curvature of the blood vessel.

SUMMARY

The disclosed embodiments include a balloon catheter that includes a balloon, an outer shaft joined to a proximal end of the balloon, an inner shaft disposed within a lumen of the outer shaft and joined to a distal end of the balloon, and a reinforcement member disposed between the outer shaft and the inner shaft. The inner shaft includes a proximal variant portion and a distal variant portion, the distal variant portion being distal of the proximal variant portion. An outer diameter of the proximal variant portion is larger than an outer diameter of the inner shaft between the proximal variant portion and the distal variant portion. An outer diameter of the distal variant portion is larger than an outer diameter of the inner shaft between the proximal variant portion and the distal variant portion. The reinforcement member includes a bulged portion configured to move in an axial direction between the proximal variant portion and the distal variant portion to make contact with at least one of the proximal variant portion and the distal variant portion.

The bulged portion may move between the proximal variant portion and the distal variant portion in the axial direction. Therefore, the degree of freedom of the reinforcement member is not lost. As a result, even in a case where the balloon catheter is curved, the reinforcement member will not be forcibly restrained. Thus, risk of bending in the middle of the balloon catheter is reduced. In addition, the range of motion of the reinforcement member is restricted because the bulged portion moves in the axial direction between the proximal variant portion and the distal variant portion of the inner shaft. Therefore, the maneuverability of the balloon catheter is fully retained. When an operator further pushes the balloon catheter distally, the bulged portion of the reinforcement member makes contact with the distal variant portion, allowing a pushing force exerted by the operator to be transmitted to the distal end of the balloon catheter. Further, when an operator pulls the balloon catheter proximally, the bulged portion of the reinforcement member makes contact with the proximal variant portion, allowing the balloon catheter to be quickly removed from the patient.

Further, the inner shaft has a proximal shaft part formed of a resin, and a distal shaft part that is joined to a distal end of the proximal shaft part and is formed of a resin softer than the resin of the proximal shaft part. At least one of the proximal variant portion and the distal variant portion is formed so that (i) a proximal end of the distal shaft part covers the distal end of the proximal shaft part, or (ii) the distal end of the proximal shaft part covers the proximal end of the distal shaft part.

Because the resin hardness of the inner shaft is softer toward the distal end, a pushing force (by means of the reinforcement member as well as the inner shaft) is improved. Further, the distal variant portion and/or the proximal variant portion may be easily formed because these members need not be produced using a separate member. By this, the manufacturing process of the balloon catheter is simplified. In addition, a conventional shaft part formed with a harder resin tends to undergo a so-called kinking more easily. Therefore, the kink resistance of the disclosed embodiments is improved by arranging the reinforcement member between the inner shaft and the outer shaft part.

A coil body may be disposed in at least one of the proximal variant portion and the distal variant portion in order to improve the rigidity of these members. The coil body may include a metal wire. Thus, inclusion of the coil body in the distal variant portion improves a pushing force of the balloon catheter. Additionally, inclusion of the coil body in the proximal variant portion allows the balloon catheter to be removed quickly from the patient.

BRIEF DESCRIPTION OF THE DRAWINGS

FIGS. 3A and 3B are partial enlarged cross-sectional views of the balloon catheter of FIG. 1: FIG. 3A shows a state where the balloon catheter is pushed; FIG. 3B shows a state where the balloon catheter is pulled.

DETAILED DESCRIPTION OF EMBODIMENTS

The present disclosure shall not be limited to the embodiments provided below, and modifications in design can appropriately be made. It is also noted that in FIGS. 1 to 8, the left side of the figures corresponds to the distal end side (the front end side) which is to be inserted into the body, and the right side of the figures corresponds to the proximal end side (the back end side) which is to be operated by an operator, such as a physician.

Figure 1:
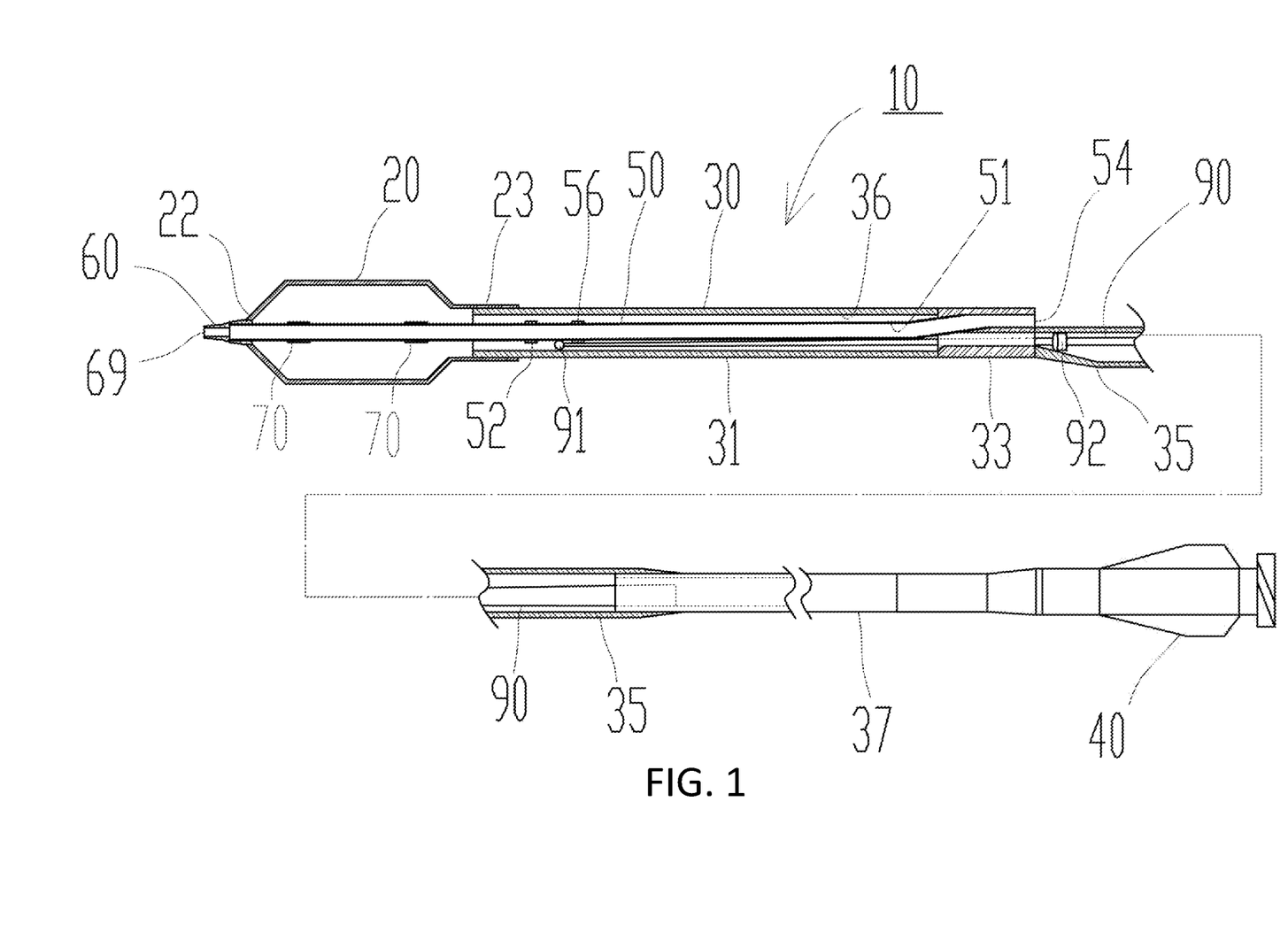
FIG. 1 is a schematic illustration of a balloon catheter according to disclosed embodiments.

As shown in FIG. 1, the balloon catheter 10 may be used for treating, for example, a stenosis site inside a blood vessel of a patient's heart. The balloon catheter 10 may comprise a balloon 20, an outer shaft 30, a connector 40, an inner shaft 50, a tip 60 and a core wire 90. The core wire 90 may function as a reinforcement member.

The balloon 20 may be used to expand a stenosis site, and the balloon 20 may be formed of a resin. Further, the balloon 20 may have a distal end attachment part 22 in the distal end side, and a proximal end attachment part 23 in the proximal end side. The distal end attachment part 22 may be joined to the distal end of the inner shaft 50 through the tip 60, and the proximal end attachment part 23 may be joined to the distal end of the outer shaft 30.

The outer shaft 30 may be used to feed a fluid through the balloon catheter 10, and the outer shaft 30 may form a tubular member which constitutes an inflation lumen 36 for feeding the fluid. Further, the outer shaft 30 has a distal end outer shaft part 31, a guide wire port portion 33, a middle outer shaft part 35, and a proximal end outer shaft part 37 in order from the distal end side to the proximal end side. The guide wire port portion 33 corresponds to a position in which the distal end outer shaft part 31, the middle outer shaft part 35, and the inner shaft 50 are joined.

The inner shaft 50 may be inserted into the distal end outer shaft part 31, and the inflation lumen 36 may be formed between the distal end outer shaft part 31 and the inner shaft 50. Moreover, the proximal end outer shaft part 37 may comprise a metal tubular member (referred to as a hypotube). In addition, the distal end of the proximal end outer shaft part 37 may be inserted into and joined to the proximal end of the middle outer shaft part 35, as shown in FIG. 1. Further, the connector 40 is attached to the proximal end of the proximal end outer shaft part 37. Accordingly, when a liquid for expanding the balloon 20 (such as a contrast agent and physiological saline) is fed from an indeflator (not shown), which may be attached to the connector 40, the liquid flows into the balloon 20 through the inflation lumen 36. Thus, the balloon 20 may expand.

The distal end outer shaft part 31 and the middle outer shaft part 35 may each form a tube formed of a resin such as, for example, polyamide, polyamide elastomer, polyolefin, polyester, and/or polyester elastomer. Further, the proximal end outer shaft part 37 may be formed of a superelastic alloy such as, for example, stainless steel (SUS304) and/or a Ni—Ti alloy.

The inner shaft 50 forms a guide wire lumen 51 for inserting a guide wire (not shown) through the balloon catheter 10. Further, the proximal end of the inner shaft 50 may be joined to the guide wire port portion 33 of the outer shaft 30 and form a proximal end side guide wire port 54. Additionally, a distal end side guide wire port 69 may be formed at the tip 60 at the distal end of the inner shaft 50.

Two marker members 70, having a cylindrical shape, may be arranged on the outer periphery of the inner shaft 50. As shown in FIG. 1, for example, the marker members 70 may be disposed inside of the balloon 20.

The inner shaft 50 may be formed of a resin such as, for example, polyethylene, polyurethane, polyamide, polyamide elastomer, polyolefin, polyester, and/or polyester elastomer. The tip 60 may be formed of a soft resin such as, for example, polyurethane and/or polyurethane elastomer. Thus, tip 60 may be formed of a softer resin than inner shaft 50. Moreover, the marker members 70 may be formed of a radiopaque metal material such as, for example, platinum and/or tungsten. However, the present disclosure is not limited to these materials, and other materials known to one of skill in the art may be used.

The core wire 90 may be attached to the inner periphery of the proximal end outer shaft part 37 at the distal end of the proximal end outer shaft part 37. The core wire 90 has a circular cross-section and may include a tapered metal wire material with a diameter that decreases toward the distal end. In addition, the core wire 90 may pass through the middle outer shaft part 35 and the guide wire port portion 33, and the core wire 90 may extend through the distal end outer shaft part 31. As shown in FIG. 1, the core wire 90 has a pressing member 92 near the proximal end of the guide wire port portion 33. When a pushing force and/or a rotating force are applied to the core wire 90, the pressing member 92 makes contact with the guide wire port portion 33, allowing the pushing force and/or the rotating force to be transmitted to the distal end outer shaft part 31 and the inner shaft 50.

Figure 2:
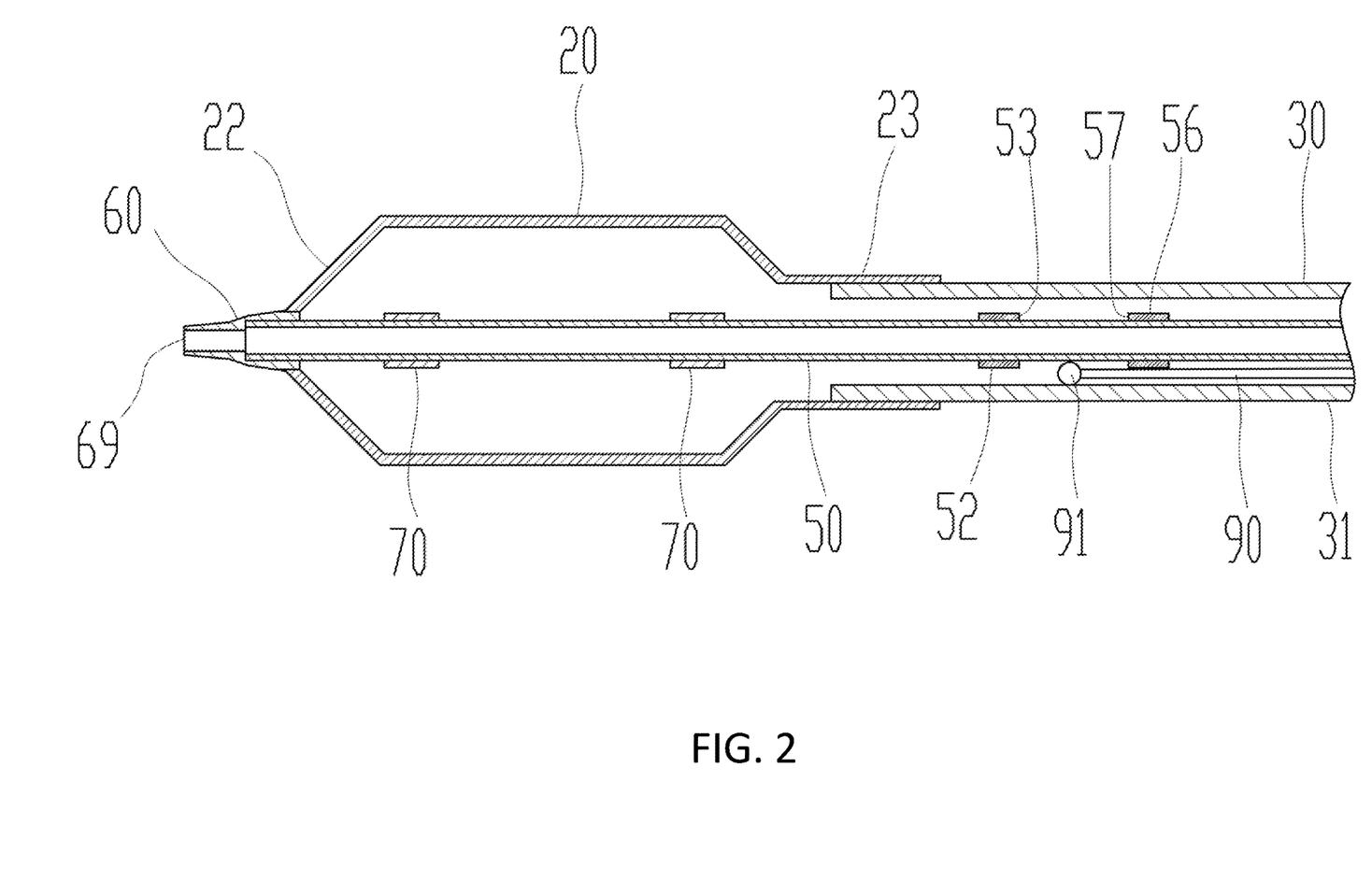
FIG. 2 is a partial enlarged cross-sectional view of the balloon catheter of FIG. 1.

As shown in FIG. 2, a cylindrical distal large-diameter member 52 and a cylindrical proximal large-diameter member 56 are each attached to the outer periphery of the inner shaft. The large-diameter members 52, 56 may be disposed proximally of the balloon 20. Additionally, the proximal large-diameter member 56 may be arranged proximally relative to the distal large-diameter member 52 and spaced from the distal large-diameter member 52.

A distal variant portion 53 may include a step part formed between a proximal end part of the distal large-diameter member 52 and the outer periphery of the inner shaft 50. A proximal variant portion 57 may include a step part formed between a distal end part of the proximal large-diameter member 56 and the outer periphery of the inner shaft 50. As shown in FIG. 2, for example, the outer diameter of the distal variant portion 53 and the outer diameter of the proximal variant portion 57 are each larger than the outer diameter of the inner shaft 50 between the distal variant portion 53 and the proximal variant portion 57.

The distal large-diameter member 52 and the proximal large-diameter member 56 may be formed of the same material as the inner shaft 50. Additionally, the distal large-diameter member 52 and the proximal large-diameter member 56 may be formed of the same material or different materials. For example, the distal large-diameter member 52 and the proximal large-diameter member 56 may be formed of a resin such as polyethylene, polyurethane, polyamide, polyamide elastomer, polyolefin, polyester, and/or polyester elastomer.

Figure 3A:
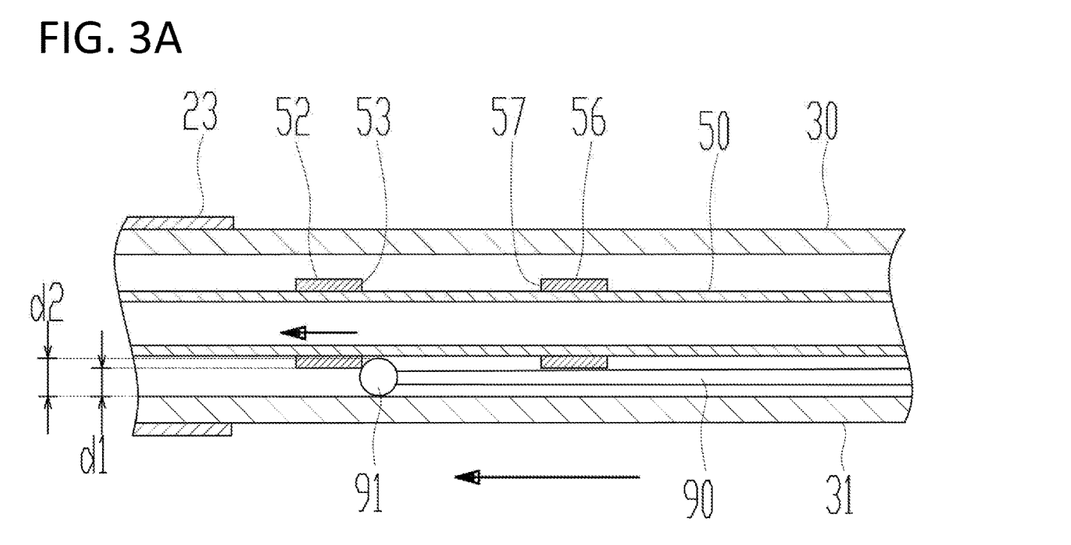
Figure 3B:
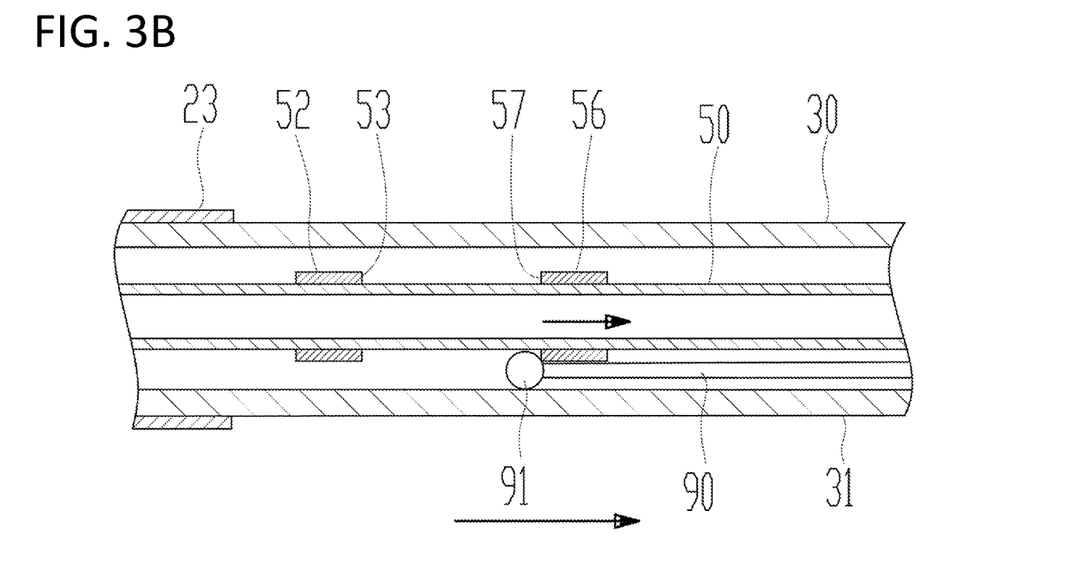

A spherical bulged portion 91 may be disposed at the distal end of the core wire 90. The bulged portion 91 may be arranged and configured to move in the axial direction between the distal variant portion 53 and the proximal variant portion 57 (FIGS. 3A and 3B). In other embodiments, the bulged portion 91 may be provided at an intermediate position along the core wire 90, although it is preferably provided at or near the distal end of the core wire 90 in view of the simplicity of the structure.

As further shown in FIG. 3A, the space (distance) d1 between the outer peripheries of the variant portions 53, 57 and the inner periphery of the outer shaft 30 may be smaller in dimension than an outer diameter d2 of the bulged portion 91 of the core wire 90 (d1<d2). Therefore, the bulged portion 91 may be capable of moving between the distal variant portion 53 and the proximal variant portion 57 to make contact with both the distal variant portion 53 and the proximal variant portion 57. The bulged portion 91 may be unable to move distally of the distal variant portion 53 and proximally of the proximal variant portion 57.

Accordingly, as shown in FIG. 3A, for example, when the balloon catheter 10 is pushed, the bulged portion 91 of the core wire 90 makes contact with the distal variant portion 53, allowing the core wire 90 to push the inner shaft 50. The pushing force applied to the balloon catheter 10 can thus be transmitted to the distal end part of the balloon catheter 10 efficiently, such that the pushing force is not lost.

Moreover, as shown in FIG. 3B, for example, when the balloon catheter 10 is pulled back, the bulged portion 91 makes contact with the proximal variant portion 57, allowing the core wire 90 to pull the inner shaft 50. Thus, the balloon catheter 10 may be removed quickly from the patient.

As described above, the bulged portion 91 may function as a reinforcement member provided at the distal end of the core wire 90 that is not fixed to the outer shaft 30 or the inner shaft 50. Therefore, the degree of freedom of the core wire 90 is retained so that, when the balloon catheter 10 passes through the inside of a curved blood vessel, a risk of bending of the core wire 90 is reduced. In addition, excessive movement of the core wire 90 within the outer shaft 30 is suppressed because the range of movement of the core wire 90 in the axial direction is restricted (between the distal variant portion 53 and the proximal variant portion 57). Therefore, maneuverability of the balloon catheter is not impaired.

The bulged portion 91 is capable of making contact with both the distal variant portion 53 and the proximal variant portion 57, as described above. However, in other embodiments, the bulged portion may be capable of making contact with one of the distal variant portion 53 and the proximal variant portion 57.

As shown in FIGS. 4A-8, the proximal variant portion 57 and the distal variant portion 53 may include various configurations.

Figure 4A:
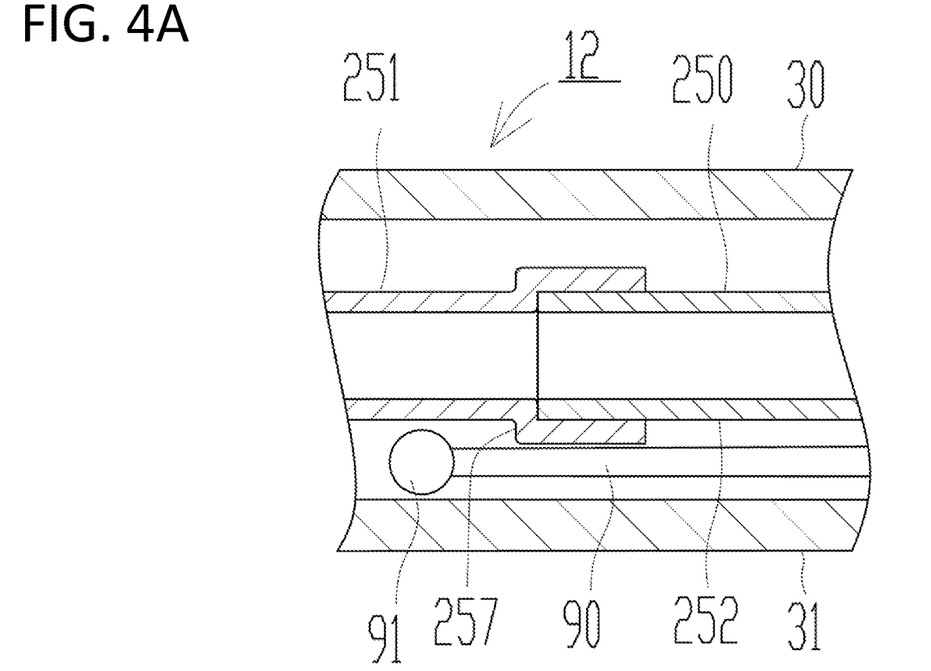
FIGS. 4A and 4B are partial enlarged cross-sectional views of modifications to the balloon catheter of FIG. 1.

As shown in FIG. 4A, balloon catheter 12 includes an inner shaft 250 that has a proximal shaft part 252 and a distal shaft part 251. The distal shaft part 251 is joined to the distal end of the proximal shaft part 252. The proximal shaft part 252 and the distal shaft part 251 may be tubular bodies having an inner diameter and an outer diameter substantially equal to each other.

The distal shaft part 251 and the proximal shaft part 252 may each be formed of a resin. The resin of the distal shaft part 251 may be softer than the resin of the proximal shaft part 252.

Further, the distal end of the proximal shaft part 252 may be inserted into the proximal end of the distal shaft part 251 so that the proximal end of the distal shaft part 251 covers the distal end of the proximal shaft part 252. Therefore, a proximal variant portion 257 is formed as a step at the distal shaft part 251.

The resin hardness of the inner shaft 250 may be softer toward the distal end of the balloon catheter 12. Therefore, a pushing force of the balloon catheter 12 is improved by the core wire 90.

It is not necessary to use a separate member to form the proximal variant portion 257. Therefore, the manufacturing process may be simplified. Furthermore, the proximal shaft part 252, when formed with a resin harder than the distal shaft part 251, may be susceptible to kinking (susceptible to bending). However, the kink resistance of the proximal shaft part 252 is improved because the core wire 90 is arranged at the same position where the proximal shaft part 252 is located.

Further, the distal end of the proximal shaft part 252 and the proximal end of the distal shaft part 251 overlap to make a connection. Thus, mutual bonding strength is increased.

Figure 4B:
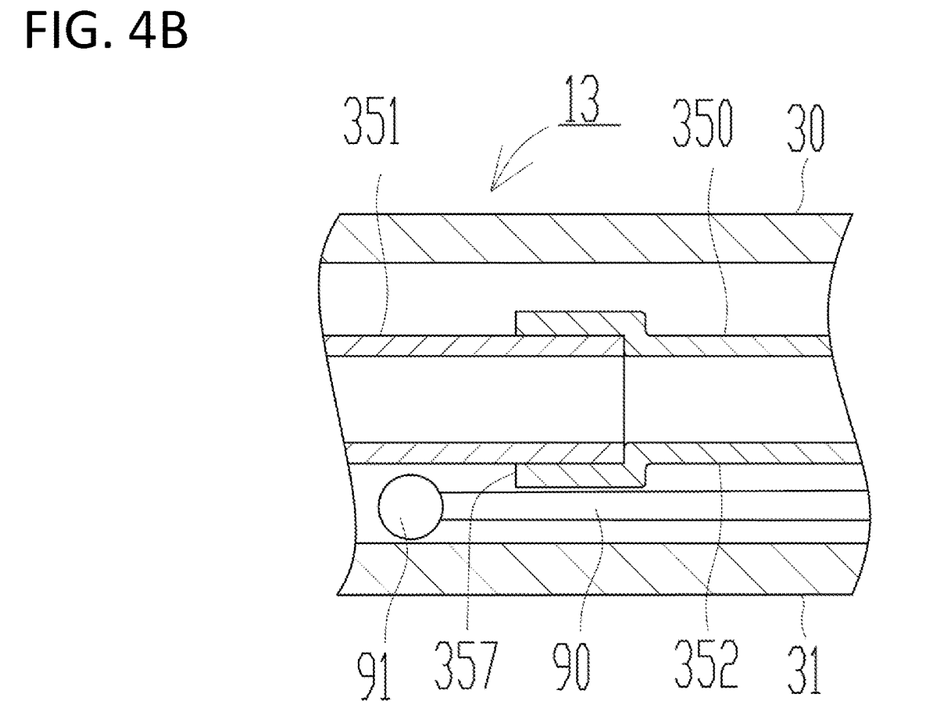

As shown in FIG. 4B, balloon catheter 13 includes an inner shaft 350 that has a proximal shaft part 352 and a distal shaft part 351. The distal shaft part 351 is joined to the distal end of the proximal shaft part 352. The proximal shaft part 352 and the distal shaft part 351 may be tubular bodies having an inner diameter and an outer diameter substantially equal to each other.

The distal shaft part 351 and the proximal shaft part 352 may each be formed of a resin. The resin of the distal shaft part 351 may be softer than the resin of the proximal shaft part 352.

Further, the proximal end of the distal shaft part 351 may be inserted into the distal end of the proximal shaft part 352 so that the distal end of the proximal shaft part 352 covers the proximal end of the distal shaft part 351. Therefore, a proximal variant portion 357 is formed as a step between the proximal shaft part 352 and the distal shaft part 351.

The resin hardness of the inner shaft 350 may be softer toward the distal end of the balloon catheter 13. Therefore, a pushing force of the balloon catheter 13 is improved by the core wire 90. Further, it is not necessary to use a separate member to form the proximal variant portion 357. Therefore, the manufacturing process may be simplified. The proximal shaft part 352, when formed with a resin harder than the distal shaft part 351, may be susceptible to kinking. However, the kink resistance of the proximal shaft part 352 is improved because the core wire 90 is arranged at the same position where the proximal shaft part 352 is located.

The distal end of the proximal shaft part 352 and the proximal end of the distal shaft part 351 overlap to make a connection. Thus, mutual bonding strength is increased.

Figure 5A:
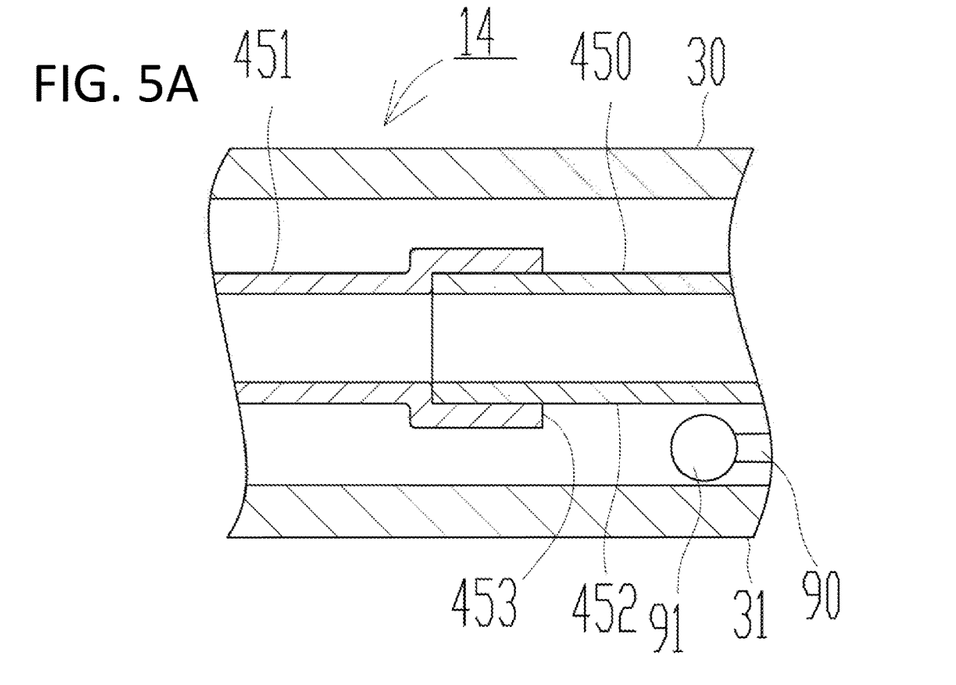
FIGS. 5A and 5B are partial enlarged cross-sectional views of modifications to the balloon catheter of FIG. 1.

As shown in FIG. 5A, balloon catheter 14 includes an inner shaft 450 that has a proximal shaft part 452 and a distal shaft part 451. The distal shaft part 451 is joined to the distal end of the proximal shaft part 452. The proximal shaft part 452 and the distal shaft part 451 may be tubular bodies having an inner diameter and an outer diameter substantially equal to each other.

The distal shaft part 451 and the proximal shaft part 452 may be formed of a resin. The resin of the distal shaft part 451 may be softer than the resin of the proximal shaft part 452.

Further, the distal end of the proximal shaft part 452 may be inserted into the proximal end of the distal shaft part 451 so that the proximal end of the distal shaft part 451 covers the distal end of the proximal shaft part 452. Therefore, a distal variant portion 453 is formed as a step between the distal shaft part 451 and the proximal shaft part 452.

The resin hardness of the inner shaft 450 may be softer toward the distal end of the balloon catheter 14. Therefore, a pushing force of the balloon catheter 14 is improved by the core wire. Further, it is not necessary to use a separate member to form the distal variant portion 453. Therefore, the manufacturing process may be simplified.

Further, the distal end of the proximal shaft part 452 and the proximal end of the distal shaft part 451 overlap to make a connection. Thus, mutual bonding strength is increased.

Figure 5B:
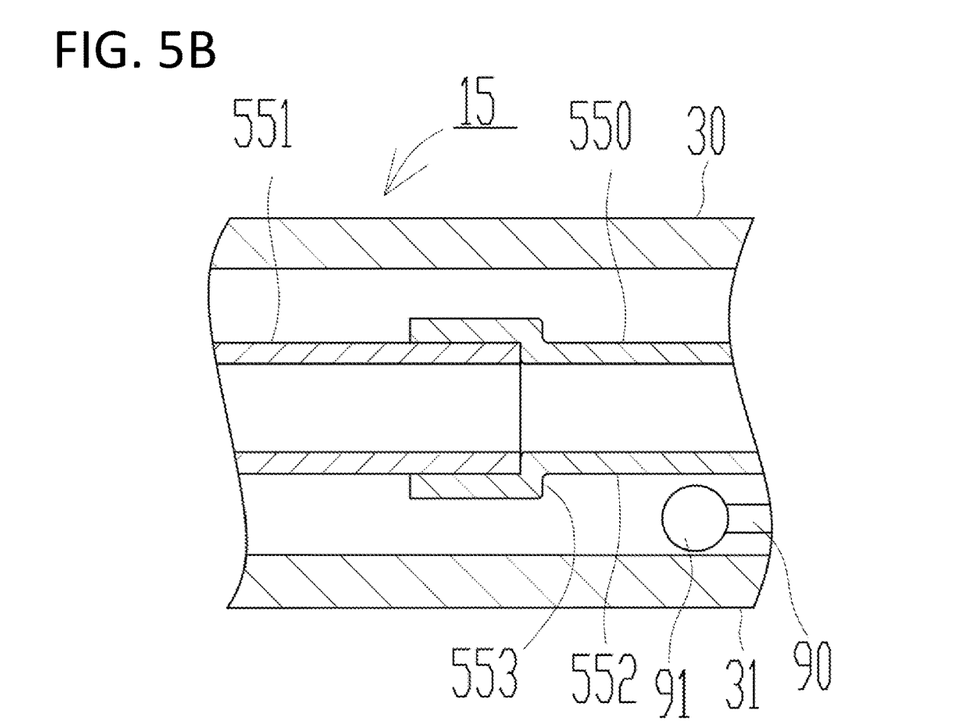

As shown in FIG. 5B, balloon catheter 15 includes an inner shaft 550 that has a proximal shaft part 552 and a distal shaft part 551. The distal shaft part 551 is joined to the distal end of the proximal shaft part 552. The proximal shaft part 552 and the distal shaft part 551 may be tubular bodies having an inner diameter and an outer diameter substantially equal to each other.

The distal shaft part 551 and the proximal shaft part 552 may each be formed of a resin. The resin of the distal shaft part 551 may be softer than the resin of the proximal shaft part 552.

Further, the proximal end of the distal shaft part 551 may be inserted into the distal end of the proximal shaft part 552 so that the distal end of the proximal shaft part 552 covers the proximal end of the distal shaft part 551. Therefore, a distal variant portion 553 is formed as a step at the proximal shaft part 552.

The resin hardness of the inner shaft 550 may be softer toward the distal end of the balloon catheter 15. Therefore, a pushing force of the balloon catheter 15 is improved by the core wire 90. Further, it is not necessary to use a separate member to form the distal variant portion 553. Therefore, the manufacturing process may be simplified.

The distal end of the proximal shaft part 552 and the proximal end of the distal shaft part 551 overlap to make a connection. Thus, mutual bonding strength is increased.

Figure 6:
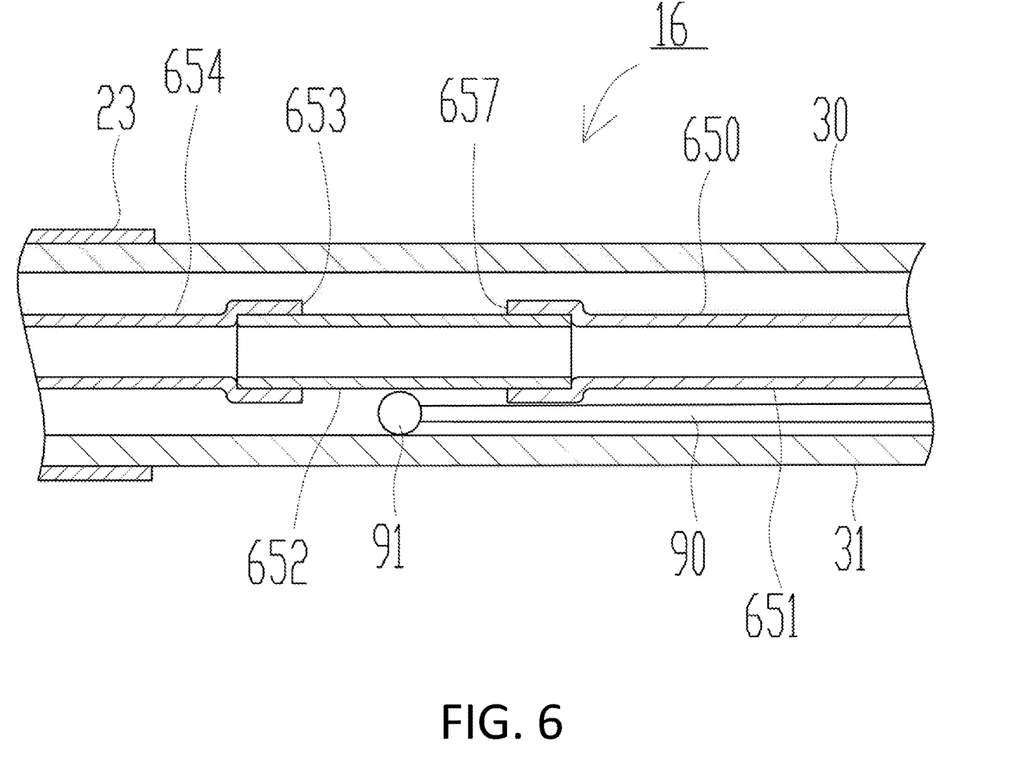
FIG. 6 is a partial enlarged cross-sectional view of modifications to the balloon catheter of FIG. 1.

As shown in FIG. 6, balloon catheter 16 includes an inner shaft 650 that has a first shaft part 651, a second shaft part 652 joined to the distal end of the first shaft part 651, and a third shaft part 654 joined to the distal end of the second shaft part 652.

The first shaft part 651, the second shaft part 652, and the third shaft part 654 may be formed of resin. The resin of the second shaft part 652 may be softer than the resin of the first shaft part 651. Additionally, the resin of the third shaft part 654 may be softer than the resin of the second shaft part 652.

The distal end of the first shaft part 651 covers the proximal end of the second shaft part 652. Therefore, a proximal variant portion 657 is formed as a step between the first shaft part 651 and the second shaft part 652. Further, the proximal end of the third shaft part 654 covers the distal end of the second shaft part 652. Therefore, a distal variant portion 653 is formed as a step between the third shaft part 654 and the second shaft part 652.

The resin hardness of the inner shaft 650 may be softer toward the distal end of the balloon catheter 16. Therefore, a pushing force of the balloon catheter 16 is improved by the core wire 90. Further, it is not necessary to use a separate member to form the distal variant portion 653 and the proximal variant portion 657. Therefore, the manufacturing process may be simplified. The first shaft part 651, when formed with a resin harder than the resin of the second shaft part 652 and of the third shaft part 654, may be susceptible to kinking (susceptible to bending). However, the kink resistance of the first shaft part 651 is improved because the core wire 90 is arranged at the same position where the first shaft part 651 is located.

In other embodiments, the proximal end of the second shaft part 652 may cover the distal end of the first shaft part 651 to form the proximal variant portion 657 and/or the distal end of the second shaft part 652 may cover the proximal end of the third shaft part 654 to form the distal variant portion 653.

Figure 7:
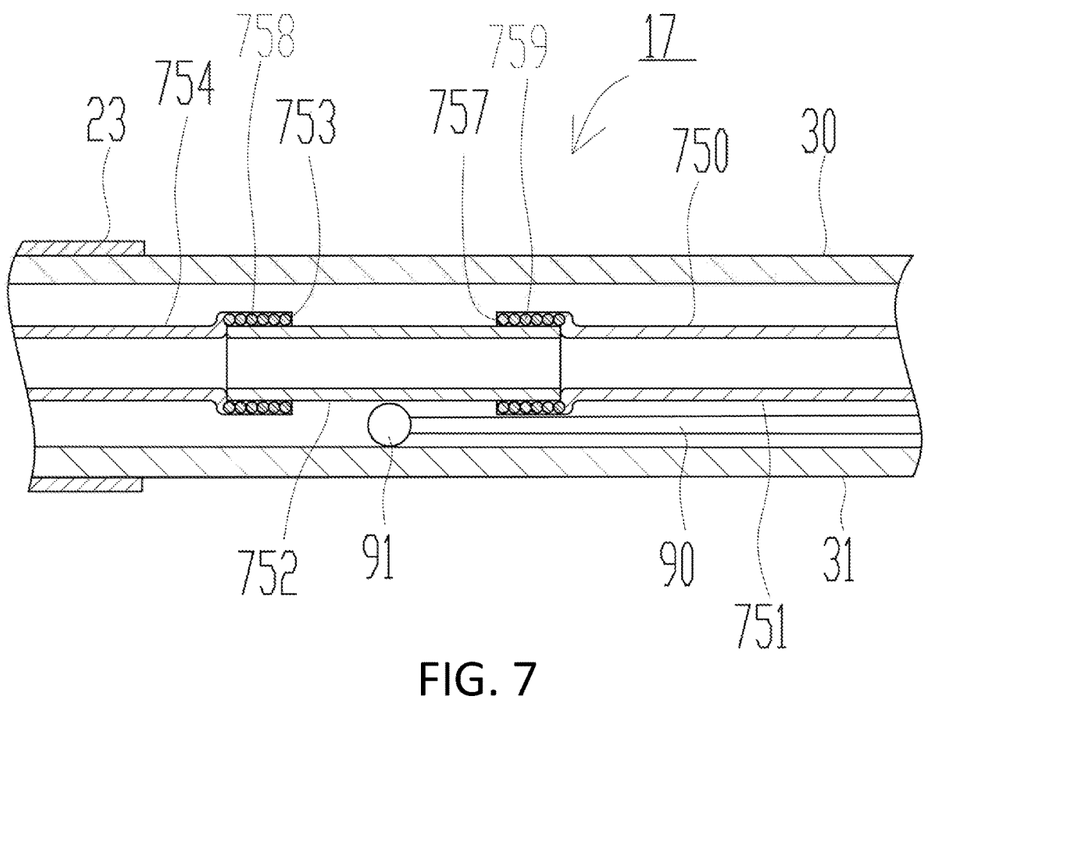
FIG. 7 is a partial enlarged cross-sectional view of modifications to the balloon catheter of FIG. 1.

As shown in FIG. 7, balloon catheter 17 includes an inner shaft 750 that has a first shaft part 751, a second shaft part 752 joined to the distal end of the first shaft part 751, and a third shaft part 754 joined to the distal end of the second shaft part 752. In addition, a proximal variant portion 757 and a distal variant portion 753 may be formed on the inner shaft 750.

A first coil body 758 may be disposed in the proximal end part of the third shaft part 754 that constitutes the distal variant portion 753. Similarly, a second coil body 759 may be disposed in the distal end part of the first shaft part 751 that constitutes the proximal variant portion 757. The first coil body 758 and/or the second coil body 759 may include a metal wire. In some embodiments, first coil body 758 may extend distally of the proximal end part of the third shaft part 754. Additionally, the second coil body 759 may extend proximally of the distal end part of the first shaft part 751. Thus, the first coil body 758 and the second coil body 759 may be disposed over the full length of the inner shaft 750.

The first coil body 758 and the second coil body 759 improve the rigidity of the distal variant portion 753 and of the proximal variant portion 757. Therefore, when the balloon catheter 17 is pushed, the bulged portion 91 of the core wire 90 makes contact with the distal variant portion 753. A pushing force exerted by the bulged portion 91 of the core wire 90 is thus adequately transmitted to the inner shaft 750, which leads to improved maneuverability of the balloon catheter 17. Further, when the balloon catheter 17 is pulled back, the bulged portion 91 of the core wire 90 makes contact with the proximal variant portion 757. A pulling force exerted by the bulged portion 91 of the core wire 90 is thus adequately transmitted to the inner shaft 750, allowing the balloon catheter 17 to be removed quickly from the patient.

In some embodiments, a coil body may be located at one of the distal variant portion 753 and the proximal variant portion 757. Thus, balloon catheter 17 may only include either first coil body 758 or second coil body 759.

Figure 8:
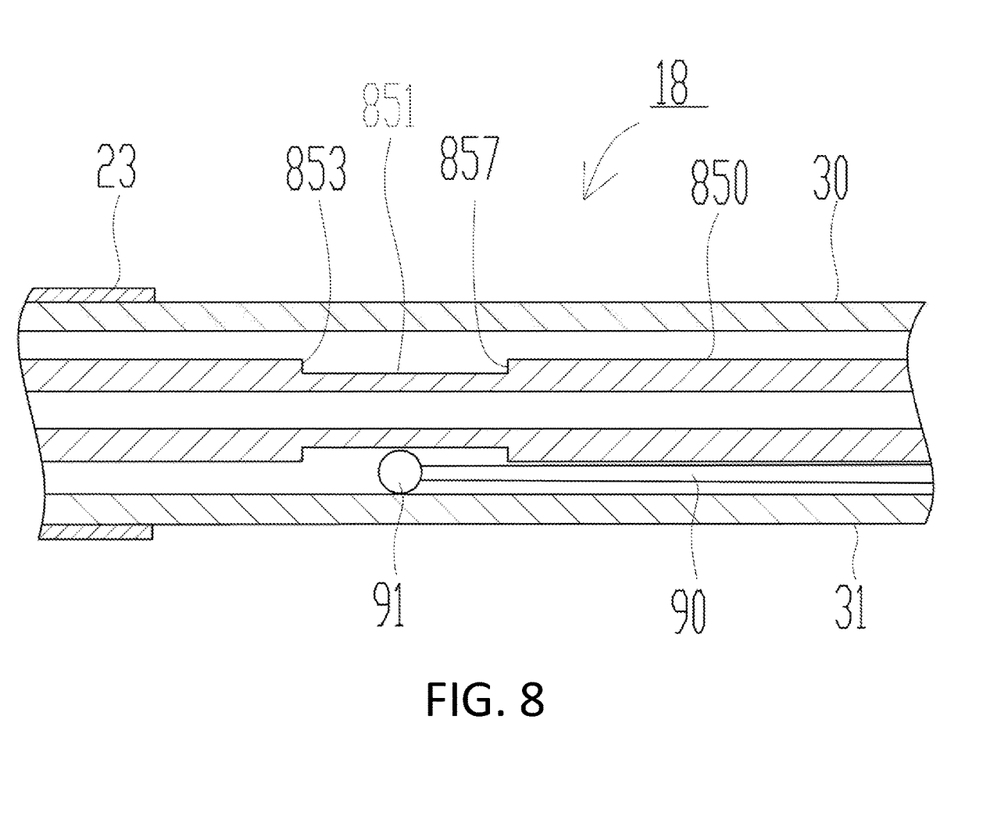
FIG. 8 is a partial enlarged cross-sectional view of modifications to the balloon catheter of FIG. 1.

As shown in FIG. 8, balloon catheter 18 includes an inner shaft 850 that has a small-diameter portion 851. The small-diameter portion 851 has a smaller outer diameter compared with the remaining portions of inner shaft 850. In addition, a distal variant portion 853 is formed at a step part at a distal end side of the small-diameter portion 851. A proximal variant portion 857 is formed at a step part at a proximal end side of the small-diameter portion 851.

The distal variant portion 853 and the proximal variant portion 857 may be formed by forming the inner shaft 850 with the same outer diameter substantially throughout the full length, and providing the small-diameter portion 851 at a desired position.

It is contemplated that additional modifications to the above-discussed embodiments may be made. For example, the distal and proximal variant portions need not be of a step-like shape, as shown in the figures, and instead may be of a tapered shape (as long as the bulged portion 91 of the core wire 90 can freely move in the axial direction within the restricted limits).

Further, the structures of the inner shaft and the outer shaft are not limited to single-layer structures, and may instead be multiple-layer structures.

Moreover, the shape of the bulged portion 91 is not limited to a globular shape, and may instead be a cylindrical shape, an elliptic shape and the like.

The bulged portion 91 may be formed by melting the distal end of the core wire 90. Alternatively, the bulged portion 91 may be formed (a) by joining a solder material (for example, an Sn—Pb alloy, a Pb—Ag alloy, an Sn—Ag alloy, an Au—Sn alloy and the like), or (b) by joining a hollow coil body with a metal wire at a distal end or at a middle position of the core wire 90.

As shown in FIGS. 1-8, the distal variant portions 53, 453, 553, 653, 753, 853 and the proximal variant portions 57, 257, 357, 657, 757, 857 may have the same outer diameter. However, the outer diameter of the distal variant portions 53, 453, 553, 653, 753, 853 may be different from that of the proximal variant portions 57, 257, 357, 657, 757, 857 as long as the distance between (i) the outer periphery of the distal variant portions 53, 453, 553, 653, 753, 853 or the proximal variant portions 57, 257, 357, 657, 757, 857 and (ii) the inner periphery of the outer shaft 30, in a radial direction, is smaller than the diameter (the maximum outer diameter) of the bulged portion 91 of the core wire 90.

What is claimed is:

1. A catheter comprising:
   an outer shaft;
   an inner shaft disposed within the outer shaft; and
   a reinforcement member disposed between the outer shaft and the inner shaft, wherein:
      the inner shaft includes a proximal variant portion and a distal variant portion that extend circumferentially around the inner shaft, the distal variant portion being distal of the proximal variant portion,
      an outer diameter of the proximal variant portion is larger than an outer diameter of the inner shaft between the proximal variant portion and the distal variant portion,
      an outer diameter of the distal variant portion is larger than the outer diameter of the inner shaft between the proximal variant portion and the distal variant portion, and
      the reinforcement member includes:
         a proximal portion extending through a space between the proximal variant portion and the outer shaft, and having a diameter smaller than a distance between an outer periphery of the proximal variant portion and an inner periphery of the outer shaft in a radial direction; and
         a bulged portion arranged between an outer surface of the inner shaft and an inner surface of the outer shaft and in direct contact with the inner surface of the outer shaft, the bulged portion having a diameter larger than both (i) the distance between the outer periphery of the proximal variant portion and the inner periphery of the outer shaft in the radial direction and (ii) a distance between an outer periphery of the distal variant portion and the inner periphery of the outer shaft in the radial direction, and being configured to move in an axial direction between the proximal variant portion and the distal variant portion until contacting with at least the distal variant portion.

2. The catheter according to claim 1, further including a coil body disposed in at least one of the proximal variant portion and the distal variant portion.

3. The catheter according to claim 2, wherein the bulged portion is at a distal end of the reinforcement member.

4. The catheter according to claim 1, wherein the bulged portion is at a distal end of the reinforcement member.

5. The catheter according to claim 1, wherein the bulged portion is unable to move distally of the distal variant portion and proximally of the proximal variant portion.

6. The catheter according to claim 1, wherein the inner shaft includes a guidewire lumen.

* * * * *